United States Patent [19]

Wang et al.

[11] Patent Number: 5,856,089
[45] Date of Patent: *Jan. 5, 1999

[54] METHOD FOR THE DETECTION OF CHROMOSOME STRUCTURAL ABNORMALITIES BY IN SITU HYBRIDIZATION TO FIXED TISSUE

[75] Inventors: Mary Ge Wang, Rockville; Albert Louis George, Jr.; Elizabeth Sophia Light, both of Gaithersburg, all of Md.

[73] Assignee: Oncor, Inc., Gaithersburg, Md.

[ * ] Notice: The terminal 18 months of this patent has been disclaimed.

[21] Appl. No.: 279,315

[22] Filed: Jul. 22, 1994

Related U.S. Application Data

[63] Continuation of Ser. No. 958,907, Oct. 9, 1992, abandoned.
[51] Int. Cl.$^6$ .............................. C12Q 1/68; C12P 19/34; C07H 21/04; C07H 21/02
[52] U.S. Cl. ................................. 435/6; 435/91.2; 435/5; 536/24.3; 536/24.32; 536/24.33; 536/23.1
[58] Field of Search .................................... 435/6, 5, 912; 536/23.1, 24.3–33, 26.6

[56] References Cited

U.S. PATENT DOCUMENTS

| | | | |
|---|---|---|---|
| 5,258,507 | 11/1993 | Cruickshank et al. | 536/24.3 |
| 5,491,224 | 2/1996 | Bittner et al. | 536/22.1 |
| 5,512,433 | 4/1996 | Cruickshank et al. | 435/6 |

FOREIGN PATENT DOCUMENTS

| | | |
|---|---|---|
| 0 430 402 | 6/1991 | European Pat. Off. . |
| WO 90/05789 | 5/1990 | WIPO . |

OTHER PUBLICATIONS

Band et al. Genes Chromosome Cancer, 1(1):48–58, Sep. 1989.
Lichter et al. Genet. Anal. Tech. Appl. 8(1):24–35, Feb. 1991.
Angerer et al. Meth. Enzymol. 152:649–661, 1987.
Matthews et al. Analytical Biochem. 169:1–25, 1988.
Drets et al. Chromosoma 78(3):371–6, 1980. Abstract.
Kawasaki, *PCR Protocols, A Guide to Methods and Applications*, Innis et al., Eds. pp.21–27 (1991).
Arnoldus et al., "Interphase Cytogenetics of Brain Tumours", *Genes Chromosomes & Cancer*, 3:101–107 (1991).
Bohlander et al., "A Method for the Rapid Sequence–Independent Amplification of Microdissected Chromosomal Material", *Genomics*, 13:1322–1324 (1992).
Creamer et al., "Detection of Chromosome Aberrations in Metaphase and Interphase Tumor Cells by In Situ Hybridization Using Chromosome–Specific Library Probes", *Hum. Genet.*, 80:235–246 (1988).
Creamer et al., "Rapid Interphase and Metaphase Assessment of Specific Chromosomal Changes in Neuroectodermal Tumor Cells by In Situ Hybridization with Chemically Modified DNA Probes", *Exp. Cell Res.*, 176:199–220 (1988).
Coussens et al., "Tyrosine Kinase Receptor with Extensive Homology to EGF Receptor Shares Chromosomal Location with Neu Oncogene", *Science*, 230:1132–1139 (1985).
Devilee et al., "Detection of Chromosome Aneuploidy in Interphase Nuclei from Human Primary Breast Tumores using Chromosomes–specific Repetitive DNA Probes", *Cancer Res.*, 48:5825–5830 (1988).
DiLella and Woo, "Cloning Large Segments of Genomic DNA Using Cosmid Vectors", *Methods in Enzymology*, 152:199–212 (1987).
Donlon et al., "Isolation of Molecular Probes Associated with the Chromosomes 15 Instability in the Prader–Willi Syndrome", *Proc. Natl. Acad. Sci. USA*, 83:4408–4412 (1986).
Emmerich et al., "Interphase Cyogenetics in Paraffin Embedded Sections from Human Testicular Germ Cell Tumor Xenografts and in Corresponding Cultured Cells", *Lab. Invest.*, 61(2)235–242 (1989).
Green and Olson, "Systematic Screening of Yeast Artificial–chromosome Libraries by use of the Polymerase Chain Reaction", *Proc. Natl. Acad. Sci. USA*, 87:1213–1217 (1990).
Hopman et al., "Detection of Numerical Chromosome Aberrations in Bladder Cancer by In Situ Hybridization", *An. J. Pathol.*, 135(6):1105–1117 (1989).
Hopman et al., "Detection of Numerical Chromosome Aberrations Using In Situ Hybridization in Paraffin Sections of Routinely Processed Bladder Cancers", *Modern Pathology*, 4(4):503–513 (1991).
Hopman et al., "In Situ Hybridization as a Tool to Study Numerical Chromosome Aberrations in Solid Bladder Tumors", *Histochemistry*, 89:307–316 (1988).
Hopman et al., "Numerical Chromosome 1, 7, 9 and 11 Aberrations in Bladder Cancer detected by In Situ Hybridization", *Canc. Res.*, 51:644–561 (1991).
Kallioniemi et al., "ERBB2 Amplification in Breast Cancer Analyzed by Fluorescence In Situ Hybridization", *Proc. Natl. Acad. Sci. USA*, 89:5321–5325 (1992).
Kawasaki, *PCR Protocols, A guide to Methods and Applications,*, Innis et al., Eds. p. 21, (1991).
Knoll et al., "Angelman Syndrome: Three Molecular Classes Identified with Chromosome 15q11q13–specific DNA Markers", *Am. J. Hum. Genet.*, 47:149–155 (1990).
Kwiatkowski et al., "Rapid Identification of Yeast Artificial Chromosome Clones by Matrix Pooling and Crude Lysate PCR", *Nucl. Acids Res.*, 18:7191–7192 (1991).
Meltzer et al., "Establishment of Two New Cell Lines Derived From Human Breast Carcinomas with HER–2/neu Amplification", *Br. J. Cancer*, 63:727–735 (1991).

(List continued on next page.)

*Primary Examiner*—Stephanie W. Zitomer
*Assistant Examiner*—Dianne Rees
*Attorney, Agent, or Firm*—Glenn E. Karta

[57] ABSTRACT

The present invention is directed to in situ hybridization methods using nucleic acid probes for single copy sequences for detecting chromosomal structural abnormalities in fixed tissue obtained from a patient suspected of having a chromosomal structural abnormality.

42 Claims, 5 Drawing Sheets

OTHER PUBLICATIONS

Mukherjee et al., "Detection and Analysis of Origin of i(12P), a Diagnostic Marker of Human Male Germ Cell Tumors, by Fluorescence In Situ Hybridization", *Genes, Chromosomes & Cancer*, 3:300–307 (1991).

Nagai et al., "Detection of Papillomavirus Nucleic Acids in Genital Precancers with the *In Situ* Hybridization Technique", *Int. J. of Gynecol. Pathol.*, 6:366–379 (1987).

Nicholls et al., "Restriction Fragment Length Polymorphisms Within Proximal 15q and Their Use in Molecular Cytogenetics and the Prader–Willi Syndrome", *Am. J. Med. Genet.*, 33:66–77 (1989).

Nuovo and Silverstein, "Comparison of Formalin, Buffered Formalin, and Bouin's Fixation on the Detection of Human Papillomavirus Deoxyribonucleic Acid from Genital Lesions", *Laboratory Investigation*, 59(5):720–724 (1988).

Nuovo et al., "In Situ Hybridization Analysis of Human Papillomavirus DNA Segregation Patterns in Lesions of the Female Genital Tract", *Gynecologic Oncology*, 36:256–262 (1990).

Oncor, Inc., "Chromosome in Situ Kit Instruction Manual" pp. 1–12 (1991).

Oncor, Inc., "Chromosome In Situ Hybridization Systems" Ed. 2, pp. 1–18 (1992).

Oncor, Inc., "Molecular Cytogenetics Bibliography", Version 2.0, 9 pages (1991).

Poddighe et al., "Interphase Cytogenetics of Tumors", *J. of Pathology*, 166:215–224 (1992).

Rappolee et al., "Wound Macrophages Express TGF–α and Other Growth Factors in Vivo: Analysis by mRNA Phenotyping", *Science*, 241:708–712 (1988).

Schwab et al., "Amplified DNA with Limited Homology to myc Cellular Oncogene is Shared by Human Neuroblastoma Cell Lines and A Neuroblastoma Tumour", *Nature*, 305:245–248 (1983).

Schwab et al., "Chromosomes Localization in Normal Human Celss and Neuroblastomas of a Gene Related to c–myc", *Nature*, 308:288–291 (1984).

Seizinger et al., "Report of the Committee on Chromosome and Gene Loss in Human Neoplasia", *Cytogenet. Cell Genet.*, 58:1080–1096 (1991).

Slamon et al., "Identification and Characterization of the Protein Encoded by the Human N–myc Oncogene", *Science*, 232:768–772 (1986).

Soloman et al., "Chromosome Aberrations and Cancer", *Science*, 254:1153–1160 (1991).

Thompson, F.H., "Cytogenetic Methodological Approaches and Findings in Human Solid Tumors", *The ACT Cytogenetics Laboratory Manual, Second Edition*, Chapter 10, pp. 451–454 (1991).

van Dekken et al., "Cytogenetic Analysis of Human Solid Tumors by In Situ Hybridization with a set of 12 Chromosome–specific DNA Probes", *Cyogenet. Cell Genet.*, 54:103–107 (1990).

van Dekken et al., "Targeted Cytogenetic Analysis of Gastric Tumors by In Situ Hybridization with a set of Chromosome–specific DNA Probes", *Cancer*, 66(3):491–497 (1990).

van Dilla and Deaven, "Construction of Gene Libraries for Each Human Chromosome", *Cytometry*, 11:208–218 (1990).

Viegas–Pequignot et al., "Detection of 1q Polysomy in Interphase Nuclei of Human Solid Tumors with A Biotinylated Probe", *Hum. Genet.*, 81:311–314 (1989).

Walt et al., "Supernumerary Chromosome 1 in Interphase Nuclei of Atypical Germ Cells in Paraffin–Embedded Human Seminferous Tubules", *Lab. Invest.*, 61(5):527–531 (1989).

Wong et al., "Gene Amplification of c–myc and N–myc in Small Cell Carcinoma of the Lung", *Science*, 233:461–464 (1986).

METHOD FOR THE DETECTION OF CHROMOSOME STRUCTURAL ABNORMALITIES BY IN SITU HYBRIDIZATION TO FIXED TISSUE

This is a continuation of application Ser. No. 07/958,907 filed Oct. 9, 1992, now abandoned.

BACKGROUND OF THE INVENTION

1. Field of the Invention

The present invention is directed to in situ hybridization methods using nucleic acid probes for single copy sequences for detecting chromosomal structural abnormalities in fixed tissue obtained from a patient suspected of having a chromosomal structural abnormality. The probes can be labeled with either a radioactive or non-radioactive label.

2. Background of the Invention

On a genetic level, cancer is the result of the accumulation of multiple genetic changes on a cells DNA. Each alteration, whether an initiating or a progression-associated event, may be mediated through a gross chromosomal change and therefore has the potential to be cytogenetically visible. The common tumor chromosome aberrations are generally classified as structural or numerical. Structural alterations include translocations, inversions, deletions, insertions and amplifications, whereas numerical abnormalities are losses or duplications of whole chromosomes. Tumors analyzed for chromosome aberrations are broadly classified by cytogeneticists as hematological, which include leukemias and lymphomas or solid which include carcinomas and sarcomas.

Two classes of genes are implicated in cancer. Some cellular genes (the proto-oncogenes) can be activated by dominant mutations. A proto-oncogene can be converted from a normal cellular gene to an oncogene by a variety of submicroscopic events including point mutations, small insertions and deletions and juxtaposition to other chromosome sequences. This last event can be visualized cytogenetically as a translocation or inversion.

The second type of tumor genes, often referred to as tumor suppressor genes, has been isolated to date only from solid tumors. Like oncogenes, these are also normal cellular genes. However, tumor suppressor genes contribute to oncogenicity through their loss rather than through their activation, and both copies must be inactivated for tumor formation to occur. Again, there are a variety of submicroscopic mutational mechanisms by which this can occur. These are detectable at the DNA level as loss of constitutional heterozygosity in tumor DNA. Loss of the entire gene, the region of the chromosome, or even the entire chromosome will also achieve this end, and in the case of a tumor suppressor gene these chromosome deletions and losses may be detected cytogenetically.

The prognosis of malignant or premalignant lesions is in many cases correlated with the quantitative and structural aberrations in the genomic content of the disease. For example, the N-myc gene, while not a classic proto-oncogene in that it does not have a homolog carried by an acutely transforming retrovirus, is grouped with the proto-oncogenes, because of its homology with C-myc. The N-myc gene was first identified in human neuroblastoma cell lines where homogeneously staining regions (HSR) on chromosomes or double minute (DM) chromosomes were frequent. In these cell lines there is a 25 to 700-fold amplification of the N-myc gene. Amplification and/or increased expression of this gene has been found in untreated primary human neuroblastomas, retinoblastomas, glioblastomas, leukemias and carcinomas, such as small cell carcinoma of the lung. Amplification of the gene in primary neuroblastomas was found to correlate strongly with rapid disease progression and poor clinical prognosis, independent of disease stage at diagnosis. Thus, amplification of the N-myc gene appeared to be more prognostic than clinical staging of the disease.

ERBB2 (Her-2/neu) oncogene, which codes for a 185 kDa transmembrane growth factor receptor, is amplified and/or expressed in 15%–25% of breast carcinomas. Association of ERBB2 amplification and over-expression with rapid proliferation, low estrogen receptor content, and high grade of ductal carcinomas suggests that this oncogene plays an important role in the progression of breast cancer. Therefore, techniques such as flow cytometry (FCM), karyotyping and molecular techniques have been developed for the detection and characterization of such genetic changes, which may be central to the initiation and progression of neoplasms.

Flow cytometric (FCM) and morphometric analyses of cells isolated from fresh tumors or nuclei isolated from paraffin blocks have become methods for a rapid and objective screening of malignant tumors to determine the DNA index of the cells. An increase in the DNA index of certain malignancies is regarded as a prognostic parameter. Although these techniques allow the estimation of the total DNA content of large cell populations, no information about specific chromosome aberrations can be obtained and the technique cannot detect minor quantitative DNA changes.

Karyotyping of tumor cells on the other hand has been described as a more objective approach allowing a more precise determination of numerical and/or structural chromosome defects. Chromosome analysis of cancer cells by karyotyping (metaphase cytogenetics) facilitates the identification of small deviations in chromosome content and chromosome structure. However, chromosome analysis of solid cancers is in general only possible after the previous culturing of the isolated tumor cells which may result in a selective growth of cells with the highest mitotic index and loss of chromosome material. Growth of biopsy tissue under tissue culture conditions is not advantageous because the tumor contains some normal cells and it has been observed that normal cells grow faster in such conditions. Thus one cannot make an accurate determination of the percentage of tumor cells to normal cells in the biopsy. Furthermore, such analyses are often hampered by the small number of recognizable metaphases, the lack of chromosome spreading, poor banding quality, and a condensed or fuzzy appearance of the chromosomes.

The multiple molecular techniques, such as DNA sequencing, Southern and Northern Blotting, RFLP analysis and PCR make it possible to study genes, their copy number, structure and the regulation of their expression. These techniques have identified different genes involved in cancers, like proto-oncogenes and tumor suppressor genes. Although the sensitivity of these molecular techniques is high, partially as a result of the large amount of starting material, no information is obtained at the single cell level, and heterogeneity within a tumor is often difficult to detect.

It is desirable in the diagnosis of cancer to maintain the structure of the tissue taken in the biopsy so as to be able to clearly identify the tumor cells from the normal cells. In particular, it would be advantageous to observe the rare tumor cell which has invaded the normal tissue in the biopsy. However, this is not possible with current methods and accordingly, determination of the penetration of the tumor into the normal tissue for diagnostic purposes is not possible.

In situ hybridization (ISH) has been developed to overcome the limitations of FCM, karyotyping and molecular genetics. The term "interphase cytogenetics" refers to the cytogenetic analysis by means of ISH applied to non-mitotic cells. The use of chromosome specific repetitive DNA probes in combination with the ISH technique enables the detection of numerical and large structural chromosome aberrations in both metaphase spreads and interphase nuclei. However, such repetitive DNA probes are not specific for the particular gene that is interrupted or altered by the deletions, translocations, inversions or amplifications. Thus detection of the chromosomal abnormality may not be possible if the repetitive DNA sequence being detected is not included in the chromosomal structural abnormality. Thus micro-abnormalities may not be detected.

Furthermore, these studies are routinely performed on freshly isolated tumor cells or cultured cells, rather than fixed paraffinated tissues. To date, previous hybridization studies have been used on cell lines, disassociated fresh tissue or frozen tissue sections. However, typically in the clinical setting it is not always possible to work on biopsy tissue as soon as it is available, since frequently, the only tumor tissue available is paraffin embedded tissue. Furthermore the use of fixed paraffinated issue is advantageous because the tissue structure is preserved. It was believed that in situ hybridization of fixed tissue could only be done with probes for repetitive DNA sequences because the fixation prevents detection of a single copy sequence. Thus single deletions of DNA sequences could not be detected.

It is evident that methods for detecting chromosomal structural abnormalities in cells in fixed tissue using single copy probes would be advantageous.

SUMMARY OF THE INVENTION

In view of the difficulties encountered with prior in situ hybridization methods for analyzing chromosomal structural abnormalities in cells from fixed tissue, there exists a need in the art for a method which can detect a chromosomal structural disorder with a single copy probe in fixed tissue.

The present invention has advantages over the prior art methods of diagnosing chromosomal structural abnormalities in cells from fixed tissue, including providing clear-cut positive/negative results and detection of the abnormality with a far greater accuracy.

In one of its method aspects, this invention is directed to a method for detecting a chromosome structural abnormality in a cell derived from a fixed tissue sample obtained from a patient suspected of having a chromosome structural abnormality which method comprises the steps of obtaining a fixed tissue sample from said patient; digesting the fixed tissue sample with an effective amount of proteinase; performing in situ hybridization on cells obtained from the digested fixed tissue sample with probes to single copy sequences in the critical chromosomal region; comparing the signal pattern of the probes to the tissues to a predetermined signal pattern for the probes obtained from performing in situ hybridization on cells having a normal critical chromosome region; and detecting a chromosome structural abnormality in said critical chromosomal region of the patient's cells.

In another of its method aspects, the method of this invention further comprises pretreating the fixed tissue sample with an effective amount of sodium bisulfite.

In one of its compositional aspects, this invention is directed to single copy probes selected from the group consisting of MYCN-113F7, ERB-5H8, ERB-7E11, ERB/Her-25A12 and ERB/Her-2F11.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 1 illustrates the signal pattern of the chromosome alpha satellite DNA probe to human placental tissue or liver tissue by in situ hybridization.

DETAILED DESCRIPTION OF THE INVENTION

Figure 1A:
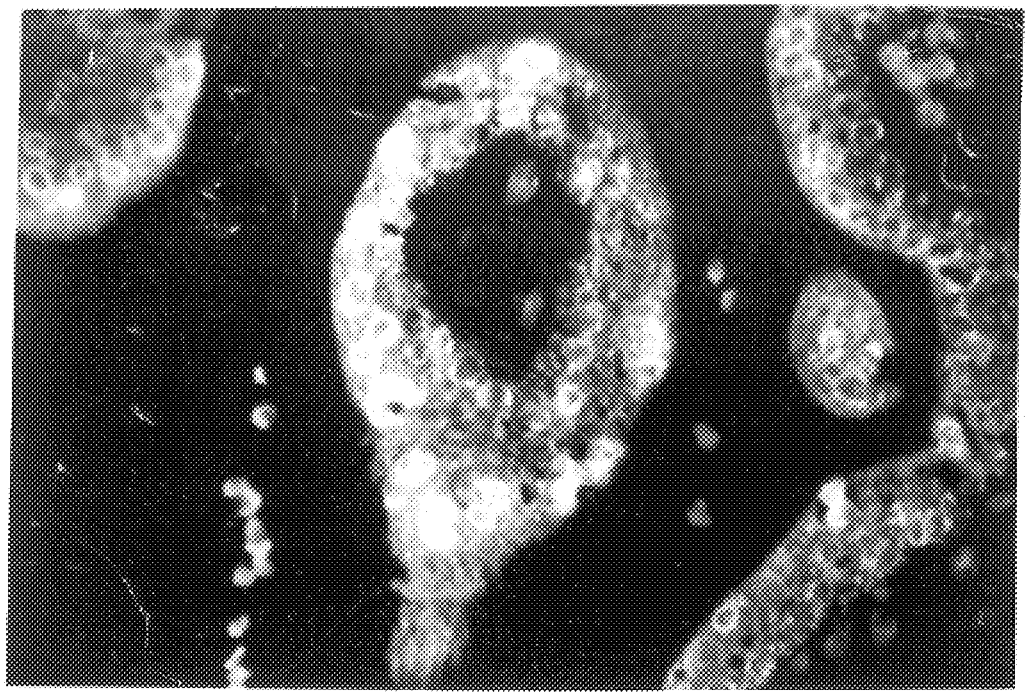
FIG. 1A is human placental tissue without sodium bisulfite.
Figure 1B:
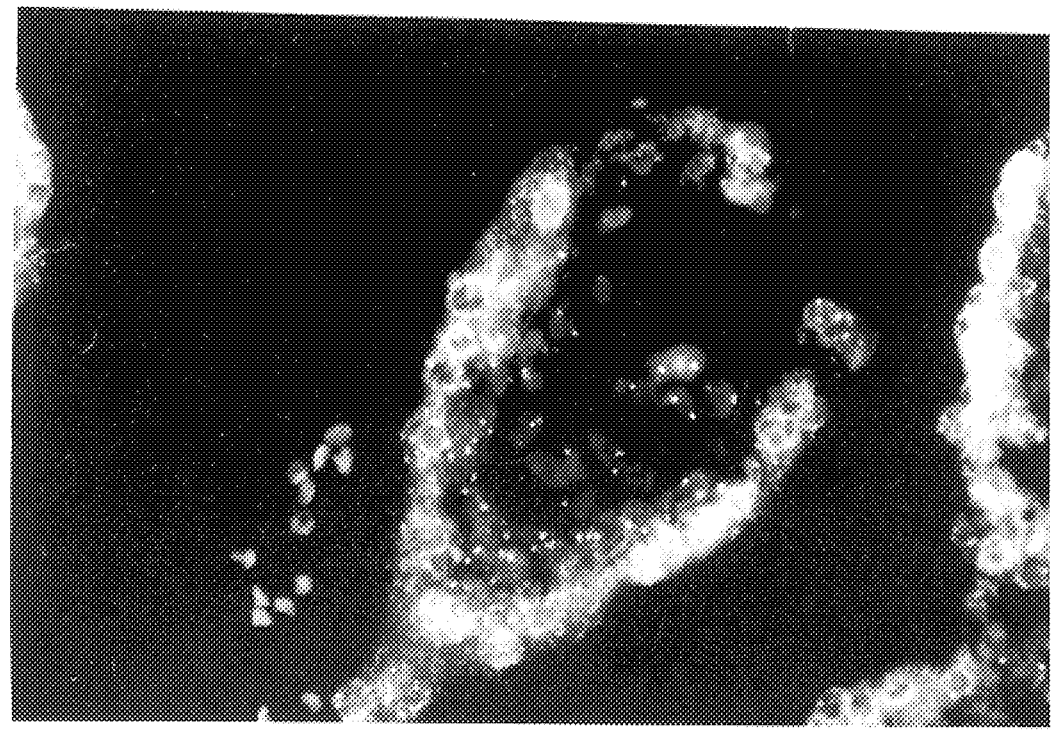
FIG. 1B is the same tissue after treatment with sodium bisulfite.
Figure 1C:
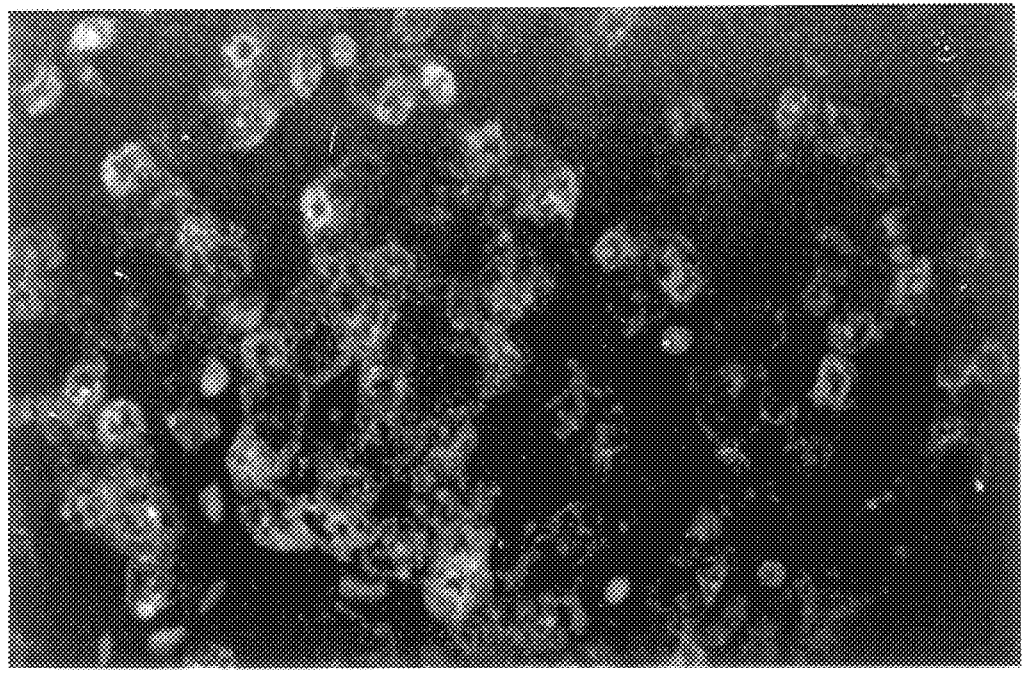
FIG. 1C and 1D is liver tissue without or with sodium bisulfite treatment, respectively.
Figure 1D:
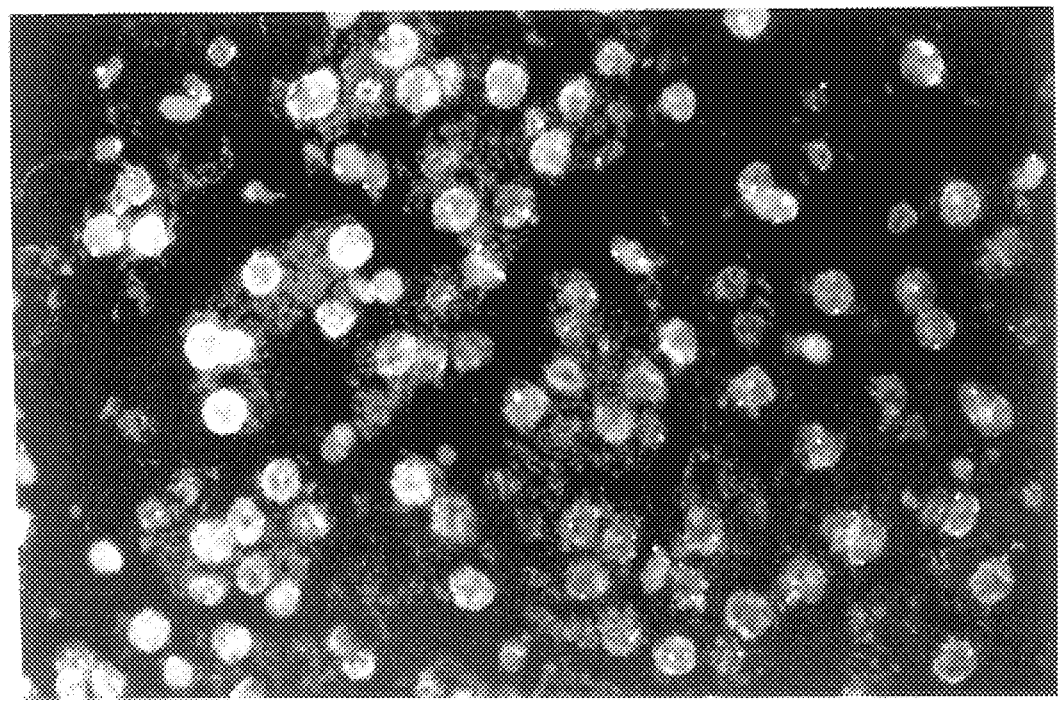

This invention generally relates to in situ hybridization methods for the identification of chromosomal structural abnormalities in fixed tissue using probes for single copy sequences. However, prior to discussing this invention in further detail the following terms will first be defined.

1. Definitions:

As used herein the following terms have the following meanings:

"Fixed tissue" means biopsy tissue which has been preserved by placing it into formalin, buffered formalin, paraformaldehyde, or equivalent preservation solutions. In some cases the fixed tissue will also be placed in paraffin in preparation for cutting with a microtome.

"Probe for a single copy sequence" means a probe containing either single or double stranded DNA or RNA which is complementary to and accordingly binds with single copy DNA sequences in the critical chromosomal region. It is contemplated that the probe for a single copy sequences may contain some repetitive DNA sequences. However, such repetitive DNA sequences will be competed out under the conditions disclosed herein for in situ hybridization such that the probe will only bind to the complementary single copy DNA sequence. Probes suitable for in situ hybridization are preferably in the range of 1,000 to $1 \times 10^6$ nucleotides long, more preferably $1 \times 10^4$ to $2 \times 10^5$ nucleotides long. Even more preferably, the probes are MYCN-113F7; ERB-5H8; ERB-7E11, ERB/Her-25A12; and ERB/Her-2F11.

A "probe for repetitive DNA sequences" means a probe containing either single or double stranded DNA or RNA, which is complementary to and accordingly binds with repetitive DNA sequences such as Alu, LINES, variable number tandem repeats, di-, tri- and tetrameric repeats and alpha-satellite DNA sequences.

"The critical chromosomal region" is that region of the human chromosome which is associated with a specific chromosomal structural abnormality related to a disease condition, such as cancer, or a genetic disease. Suitable critical chromosomal regions may be 1p36; 2p; 3p12–14; 3p21–25; 4q11–32; 10q; 11p15; 11q13; 13q12–22; 16q22–24; 17p12–13; 17q; 18q and 22q. Preferably this region includes either the N-myc (2p) or Her-2/neu (17q) chromosomal regions.

The term "chromosomal structural abnormality" refers to alterations in the DNA of the chromosome arising from translocations, deletions, inversions, duplications or amplifications. It is contemplated that this method may be used to detect point mutations and therefore a chromosomal structural abnormality may include point mutations in the critical chromosomal region.

"Proteinase" means any proteinase capable of digesting mammalian tissue. Preferably, the proteinase is proteinase K.

2. Methodology

A. Probes

Probes useful in isolating probes for a single copy sequence for use in in situ hybridization may be obtained by a variety of technical methods known in the art. One method utilizes chromosomal microdissection of the critical chromosomal region, followed by digestion with an appropriate restriction enzyme, and ligation of the resulting fragments into a vector which has been appropriately digested, or by direct PCR amplification of the microdissected fragment. Microdissection as used herein refers to the microscopic dissection of a region of a chromosome. Probes may also be generated by direct oligonucleotide synthesis from known sequences, for example using an Applied Biosystems (Foster City, Calif.) DNA Synthesizer (Model 380b). Probes can be isolated randomly from a suitable library and analyzed through RFLP analysis or in situ hybridization methods disclosed below to determine whether they are suitable. Alternatively, if DNA probes are known which represent DNA markers in close proximity to the critical region, for example from commercially available sources such as the American Type Culture Collection (ATCC), all or part of these DNA probes can be used to isolate critical region DNA probes which contain all or part of the probe as well as DNA from the critical region.

Sequence tagged sites (STSs) for PCR screening of the libraries can be developed using DNA from appropriate probes which have been isolated and sequenced by standard methods. A preferred method of sequencing is by dideoxy sequencing, preferably using the Sequenase® version 2.0 kit (United States Biochemical Corporation, Cleveland, Ohio). STS as used herein, is a Human Genome Project-related concept which relates to the systematic development of PCR primers to various human genomic regions, designed to facilitate information exchange and dissemination.

Probes suitable for screening libraries to identify clones in the critical chromosome region may be in the range of $10 \times 10^5$ to nucleotides long, more preferably $30 \times 10^4$ to 1,000 nucleotides long, and even more preferably 10,000 to 1,000 nucleotides long. Probes to screen libraries containing DNA sequences from the critical chromosomal region may be DNA or RNA.

Probes may be directly labeled with any detectable label known in the art, including radioactive labels such as $^{32}P$, $^3H$, and $^{35}S$ by methods known in the art.

It is necessary to obtain or generate a DNA library which includes clones containing sequences in the critical region. Libraries useful for screening regions associated with the chromosomal structural disorder include any genomic library obtained from a normal individual, which library contains fragments from the critical chromosomal region. Especially useful libraries are those which utilize a vector in which large DNA fragments from the critical chromosomal region can be inserted. Examples of appropriate vectors are yeast artificial chromosomes (YACs) and cosmids. The library may be generated by any method known in the art, such as flow sorted libraries. Such libraries may be commercially available or available from particular research institutions.

Libraries may be screened using any method known in the art. One preferable method of screening YAC libraries is by PCR, using a procedure such as that of Green and Olson (*Proc. Natl. Acad. Sci.*, 87:1213–1217) followed by a final positive colony identification using a PCR based matrix pooling strategy such as that employed by Kwiatkowski et al. (1991, *Nucl. Acids. Res.*, 18:7191–7192). Another preferable method is screening by hybridization on conventional Southern Blots. Transformed cells can be stamped onto a nitrocellulose or nylon membrane, transferred to an agar plate and then pooled. DNA can then be isolated from these pooled cells, digested using a restriction enzyme, and run on an acrylamide or preferably an agarose gel and blotted. Alternatively, cells on the membrane may be grown, lysed and treated by methods known in the art so that hybridization with the probe can be conducted.

Cosmid libraries may be screened by stamping transformed cells on nitrocellulase or nylon membranes and transferring the membranes to an agar plate for incubation overnight. The cells can then be lysed on the membrane, denatured, and hybridized to the probe by methods known in the art.

The Southern Blots or membranes containing lysed cells can be screened with probes generated by the methods discussed above. DNA fragments from positive cells containing the vector with large chromosomal inserts can then be analyzed to determine whether they are located within the critical chromosome region by pulsed-field gel electrophoresis of the clones followed by Southern Blotting and hybridization with the original probe.

Probes suitable for use in in situ hybridization are preferably in the range of 1000 to $1 \times 10^6$ nucleotides long, more preferably $1 \times 10^4$ to $2'10^5$ nucleotides long. The ability to isolate large clones in the critical chromosome region provides better probes for in situ analysis, particularly by fluorescence in situ hybridization (FISH). Probes may be DNA or RNA. Preferably the probes are fragments from the critical chromosome region, more preferably they are from clones MYCN-113F7, ERB-5H8, ERB-7E11, ERB/Her-25A12 and ERB/Her2F11.

In a preferred embodiment, multiple probes spanning the critical chromosome region may be used. These multiple probes may be overlapping, or may be positioned with the 3' end of a first probe directly adjacent to the 5' end of a second probe. Alternatively, these probes may not span the entire critical chromosomal region, but may span a sufficient sequence to detect whether a chromosomal abnormality is present.

The probe may be labeled with a detectable marker by any method known in the art. Preferred methods for labelling probes are by random priming, end labeling, PCR and nick translation, but nick translation is preferable. For nick translation, probes may be treated with a restriction enzyme to reduce the size of the DNA, treated with DNase I, and labeled. Labeling is conducted in the presence of DNA polymerase, three unlabeled nucleotides, and a fourth nucleotide which is either directly labeled, contains a linker arm for attaching a label, or is attached to a hapten or other molecule to which a labeled binding molecule may bind (Boehringer Mannheim, Indianapolis, Ind.). Suitable direct labels include radioactive labels such as $^{32}P$, $^3H$, and $^{35}S$ and non-radioactive labels such as fluorescent markers, such as fluorescein, Texas Red, AMCA blue (7-amino-4-methyl-coumanine-3-acetate), lucifer yellow, rhodamine, and the like; cyanin dyes which are detectable with visible light; enzymes and the like.

The use of non-radioactive labels in this invention is particularly surprising because the art recognizes that such labels are less sensitive than radioactive labels and accordingly, typically require hundreds of copies of the chromosomal structural abnormality in the tissue sample being analyzed for detection of this abnormality.

Fluorescent markers may alternatively be attached to nucleotides with activated linker arms which have been incorporated into the probe. Probes may be indirectly labeled by the methods disclosed above, by incorporating a nucleotide covalently linked to a hapten or other molecule such as biotin or digoxygenin, and performing a sandwich hybridization with a labeled antibody directed to that hapten or other molecule, or in the case of biotin, with avidin conjugated to a detectable label. Antibodies and avidin may be conjugated with a fluorescent marker, or with an enzymatic marker such as alkaline phosphatase or horseradish peroxidase to render them detectable. Conjugated avidin and antibodies are commercially available from companies such as Vector Laboratories (Burlingame, Calif.) and Boehringer Mannheim (Indianapolis, Ind.).

The enzyme can be detected through a colorimetric reaction by providing a substrate and/or a catalyst for the enzyme. In the presence of various catalysts, different colors are produced by the reaction, and these colors can be visualized to separately detect multiple probes. Any substrate and catalyst known in the art may be used. Preferred catalysts for alkaline phosphatase include 5-bromo-4-chloro-3-indolylphosphate (BCIP) and nitro blue tetrazolium (NBT). The preferred substrate for horseradish peroxidase is diaminobenzoate (DAB).

B. Method

Initially, the fixed tissue is placed in paraffin for sectioning on the microtome. Alternatively, the tissue could be sufficiently frozen so that it can be cut in sufficiently thin sections on the cryostat. It has been determined that sections of 3 microns to 4 microns are preferred for in situ hybridization.

In a preferred embodiment of the present invention, sodium bisulfite is added to the fixed tissue as a pretreatment step prior to proteinase digestion and the hybridization step. The term "sodium bisulfite" means sodium bisulfite or sodium metabisulfite. Surprisingly, the addition of an effective amount of a sodium bisulfite composition (e.g., a solution of sodium bisulfite in water) has been found to be active in improving the signal upon in situ hybridization. In this regard an "effective amount of a sodium bisulfite composition" is that amount added to the tissue which is necessary to improve the signal such that a probe for single copy sequences can be detected. The amount of sodium bisulfite composition added is dependent on the type of tissue which is being pretreated and the length of time of fixation. Without being limited to any theory, it is believed that the longer the tissue has been fixed the greater the amount of sodium bisulfite composition which should be added to the tissue in the pretreatment step. Preferably, the sodium bisulfite composition is a solution of sodium bisulfite in a compatible aqueous solvent such as water, 2×SSC, and the like. More preferably, the amount of sodium bisulfite added to the compatible solvent is from about 10% to 30%. Table 1 shows the amounts of sodium bisulfite which have been determined to be effective amounts for certain tissues. One skilled in the art could readily determine the amount of sodium bisulfite to be added to a tissue not listed in Table 1 by adding various amounts of sodium bisulfite and observing the level of background remaining after in situ hybridization.

TABLE I

Chart for Pretreatment and Protein Digesting Enzyme Times for Various Tissue Types

| Tissue Type | Sodium Bisulfite Composition | | 250 µg/ml Proteinase K Solution |
|---|---|---|---|
| | Time (min.) | Concentration | Time (min.) |
| Bladder Tumor | None | | 20 |
| Cervical Tumor | 15 | 30% | 10 |
| Epididymis | 10 | 30% | 20 |
| Ileum | 10 | 10% | 20 |
| Kidney | None | | 40–80 |
| Liver | 30–60 | 30% | 40 |
| Placenta | 10–15 | 30% | 10–20 |
| Prostate | 15 | 20% | 10 |
| Testis | 10 | 10–30% | 20 |
| Tonsil | 60 | 30% | 40 |

The tissue sections are then treated with an effective amount of a proteinase. Preferably the proteinase is proteinase K available from Boehringer Mannheim. The time required for proteinase digestion of the tissue section will vary depending on the type of tissue. Certain tissue sections are more resistant to the effects of proteinase digestion than others. This may be due to the tissue type or length of time of formalin fixation. It has been found that normal tissues are more refractory to protein digestion than tumor material derived from the same tissue type. Table 1 above illustrates the time required for proteinase digestion. The length of time will vary depending on concentration and type of proteinase employed. An "effective amount of proteinase" is that amount which will digest the tissue sufficiently such that a probe for single copy sequences can be detected. One skilled in the art could readily determine the length of time required for proteinase digestion and the effective amount of proteinase required by observing the level of signal obtained with in situ hybridization.

Hybridization of the detectable probes to the cells is conducted with a probe concentration of 0.1–500 ng/µl, preferably 5–250 ng/µl. The probe concentration is greater for a larger clone.

The hybridization mixture will preferably contain a denaturing agent such as formamide, and non-specific human DNA, preferably derived from the placenta, which is used to block repeat sequences. The non-specific DNA is added at a concentration of 100 ng/µl–2 µg/µl, more preferably 0.2–1 µg/µl, and most preferably 0.25–0.5 µg/µl to compete out any repetitive portions of the probe.

The DNA in the tissues and the DNA probes are denatured either independently prior to hybridization or simultaneously. In general the denaturation is carried out by placing the tissues or DNA probes into a hybridization solution preferably containing a denaturing agent such as formamide and heating from 70° C. to 95° C. Preferably the concentration of formamide is from about 30% to 70%, more preferably 40% to 60%. The temperature at which the tissues are held in order to achieve denaturation will vary according to the concentration of the denaturation agent. Surprisingly, it has been found that probes for single copy sequences do not need to be denatured prior to placement on the denatured tissue. Therefore, in a preferred embodiment the single copy probe is not denatured prior to hybridization.

In general, hybridization is carried out at 25° C.–45° C., more preferably at 32° C.–40° C., and most preferably at 37° C.–38° C. The time required for hybridization is about 0.25–96 hours, more preferably 1–72 hours, and most preferably for 4–24 hours. Hybridization time will be varied based on probe concentration and hybridization solution content which may contain accelerators such as hnRNP binding protein, trialkyl ammonium salts, lactams, and the like. Slides are then washed with solutions containing a denaturing agent, such as formamide, and decreasing concentrations of sodium chloride or in any solution that removes unbound and mismatched probe.

The temperature and concentration of salt will vary depending on the stringency of hybridization which is desired. For example, high stringency washes may be carried out at 42° C.–68° C., while intermediate stringency may be in the range of 37° C.–55° C., and low stringency may be in the range of 30° C.–37° C. Salt concentration for a high stringency wash may be 0.5–1×SSC (0.15M NaCl, 0.015M Na citrate), while medium stringency may be 1×4×, and low stringency may be 2×–6×SSC.

The detection incubation steps, if required, should preferably be carried out in a moist chamber at 23° C.–42° C., more preferably at 25° C.–38° C. and most preferably at 37°–38° C. Labeled reagents should preferably be diluted in a solution containing a blocking reagent, such as bovine serum albumin, nonfat dry milk, or the like. Dilutions may range from 1:10–1:10,000, more preferably 1:50–1:5,000, and most preferably at 1:100–1:1,000. The slides or other solid support should be washed between each incubation step to remove excess reagent.

Slides may then be mounted and analyzed by microscopy in the case of a visible detectable marker, or by exposure to autoradiographic film in the case of a radioactive marker. In the case of a fluorescent marker, slides are preferably mounted in a solution which contains an antifade reagent, and analyzed using a fluorescence microscope. Multiple nuclei may be examined for increased accuracy of diagnosis.

It will be recognized that the above descriptions are preferred methods of carrying out the process of the present invention and that numerous variations of the above methods can be made in the process following the teachings of this invention. The various process conditions can be altered and reagents used can be changed to provide various desired or optimum operating conditions for in situ hybridization of single copy probes to fixed tissue samples.

The value of ISH on paraffin sections as compared to ISH on isolated tumor cells can be summarized as follows: (1) chromosome heterogeneity (e.g., tetraploidization) can be detected within a tumor; (2) focal tumor cell areas with chromosome aberrations can be recognized in the sections and be correlated with the histologic appearance; (3) discrimination between stromal, inflammatory cells and tumor cells is possible; and (4) no selection of cells occurs as a result of the cell disaggregation procedure.

The following examples are presented in order to more fully illustrate the preferred embodiments of the invention. They should in no way be construed, however, as limiting the broad scope of the invention.

EXAMPLE 1

Method for Isolating the N-myc Cosmid Probe

A 1.0 kb DNA fragment representative of exon 2 in the N-myc gene (ONCOR Catalog No. P2085) was used to screen a total human genomic cosmid library, ONG1.

ONG1 is a cosmid library constructed at ONCOR which has an average human insert size of 38.0 kilobase pairs. Construction of this cosmid library was as follows: High molecular weight DNA was prepared from 300.0 milliliters of peripheral blood from a Caucasian male volunteer by protocols similar to DiLella and Woo (1987) "Guide to Molecular Cloning Techniques," *Methods in Enzymology,* 152:199. The DNA was partially digested with Sau3A restriction enzyme and size fractionated in a linear NaCl gradient (DiLella and Woo, Ibid.) DNA averaging 30.0 to 45.0 kilobase pairs was ligated into the BamHI site of the SuperCos 1 (Stratagene, La Jolla, Calif.) vector utilizing protocols similar to DiLella and Wood (ibid.) The ONG1 library consists of $2.7 \times 10^5$ cosmid clones (~3.5X genome equivalent) maintained in the *E. coli* laboratory host strain DH5αmcr.

The ONG1 library was high density arrayed on nylon membranes using a Biomek 1000 Automated Laboratory workstation (Beckman Instruments, Fullerton, Calif.). The membranes are incubated overnight on agar plates to allow the transformants to grow. The colonies were lysed on the membrane; the DNA denatured and the membranes hybridized to the $^{32}$P labeled 1.0 kb DNA fragments representing exon 2 of the N-myc gene. This method identified one cosmid (MYCN-113F7) with an approximately 38 kb human insert. The cosmid was labeled with biotin-16-dUTP (Boehringer Mannheim, Indianapolis, Ind.) by nick translation.

EXAMPLE 2

Isolation of Her-2/neu Cosmid Probe

Two screening probes representing unique areas of the Her-2/neu (c-erbB-2) gene were simultaneously used to probe the chromosome 17 flow-sorted cosmid library LA17NC01 (Van Dilla et al. [1990] *Cytometry,* 11: 208) for cosmid clones.

One screening probe was a 1.091 kb cDNA sequence from the 5' end of the gene which is currently available from ONCOR for oncogene analysis on Southern Blots (Catalog No. P1720). For the other probe, cDNA sequence data (Coussens et al., [1985] *Science,* 230:1132) was used by ONCOR to design PCR primers to the distal 3' region of the gene as follows: Her 2F -5'CGGCCAAGATTCCGGGAGTTGGT 3' (SEQ ID NO:1) and Her 2G -5'TCTTGATGCCAGCAGAAGTCAGGC 3'(SEQ ID NO:2). These primers were made on a Cyclone+ (Milligen, Burlington, Mass.) automated oligonucleotide synthesizer. The reverse transcription of human RNA followed by amplification by the polymerase chain reaction (RTPCR) with the Her 2F and Her 2G primers was conducted as outlined by Kawasaki, in *PCR Protocols, A Guide to Methods and Applications,* Innis et al., Eds., Academic Press, Inc., San Diego, Calif. 21 (1991); and Rappolee et al. (1991) *Science,* 241:708. The resulting PCR product formed the second Her-2/neu probe.

The LA17NC01 library was screened by hybridization with the two Her-2/neu specific probes described above by the methods set out in Example 1 which methods are similar to DiLella and Woo (1987) "Guide to Molecular Cloning Techniques," *Methods in Enzymology,* 152:199. Six positive clones were isolated from the LA17NC01 library and fingerprinting analysis with EcoR1 and HindIII single and double restriction enzyme digests was conducted. Four overlapping cosmids (ERB-5H8, ERB-7E11, ERB/Her-25A 12, ERB/Her-2F11) were identified. These cosmids were labeled by the methods previously described in Example 1 and used collectively for fluorescence in situ hybridization (FISH).

EXAMPLE 3

Isolation of Chromosome 15 Probe

The chromosome 15 probe is a 3 member contig comprising clones 27F10, 171F12, and 162B3. These clones were isolated by the methods disclosed in U.S. Ser. No. 07/943,639, filed Sep. 11, 1992 entitled "Method for the Diagnosis of Genetic Disorders Associated with Chromosomal Abnormalities and Uniparental Disomy," Attorney Docket No. 020160-132, which is incorporated herein in its entirety. More specifically, plasmid p1R4-3R (D15511) (Nicholls et al. [1989] *Am. J. Med. Genet.*, 33:66–77; Donlon et al. [1986] *Proc. Natl. Acad. Sci. USA*, 83:4408–4412; Knoll et al. [1990] *Am. J. Hum. Genet.*, 47:149–155), was labeled with $^{32}$P and used to probe the ONG1 library by the method described in Example 1.

Cosmid clones 27F10, 171F12, and 162B3 were isolated. These cosmids were each approximately 25 kb.

EXAMPLE 4

In Situ Hybridization of Normal Tissue with Repetitive DNA Probes

Preparation of Slides

Tissue specimens were obtained after surgery or by fine-needle aspiration biopsies from patients. These tissues had been fixed in formalin, buffered formalin or paraformaldehyde by the hospital laboratory by methods known in the art. In this example, the fixed tissue was normal human placenta tissue or normal human liver tissue.

The tissue was first embedded in Paraplast (Oxford Labware Div. of Sherwood, Media, St. Louis, Mo.) and sectioned into 4 micron thick sections for hybridization on a microtome by methods known in the art. The tissues are applied to silanized slides (ONCOR, Gaithersburg, Md.) by floating the paraffin-embedded section in pure distilled water at 45° C. to 47° C.

After attaching the tissue sections to the slide, the tissue was allowed to air dry. The slides were baked at 65° C. overnight. This fixes the tissue to the slide.

The slides were next deparaffinized by soaking the slides in xylenes at room temperature (RT) for 5 minutes with gentle periodic agitation (i.e., shaking 4 to 5 times during the 5 minute period). The xylenes treatment was repeated once. Then the slides were transferred to 100% ethanol for 5 minutes. The slides were then transferred to fresh ethanol for an additional 5 minutes. The slides were agitated 2 to 3 times during each 5 minute period in ethanol. The slides were then removed from the ethanol and allowed to air dry.

Pretreatment of Tissues

One half of the slides were next pretreated to prepare the tissues for in situ hybridization. It has been found that in some cases pretreatment of the tissue with sodium bisulfite (Sigma, Catalog No. S8890, St. Louis, Mo.) prepares the tissue in such a manner that the probe signal is more easily detected.

The concentration of the sodium bisulfite composition is dependent on the type of tissue. Generally, the concentration of sodium bisulfite in water will be in the range of 10% to 30%.

In the case of the human placenta, 30% sodium bisulfite was added to the slide for 15 minutes at 43° C. The liver tissue was treated in 30% sodium bisulfite for 1 hour at 43° C. The slides were then washed in water 3 times at room temperature for 1 minute each.

The slides were dehydrated by passing the slides through a series of room temperature ethanol washes of 70%, 80%, 90% and 100% ethanol for 2 minutes at each concentration, beginning with the 70% ethanol wash. All washes were done in coplin jars. The slides were then allowed to air dry.

Protein Digesting Enzyme Treatment

All of the slides, both pretreated and not pretreated, were then placed into 250 ug/ml proteinase K (Boehringer Mannheim) in 2×SSC. The placental tissue was treated with the proteinase K solution for 15 minutes at 37° C. The liver tissue was treated with the proteinase K solution for 40 minutes at 37° C. The slides were rinsed in 3 changes of water at room temperature for 1 minute each rinse. The slides were dehydrated by passing the slides through a series of room temperature ethanol washes of 70%, 80%, 90% and 100% ethanol for 2 minutes at each concentration, beginning with the 70% wash. All washes were done in coplin jars. In some cases, slides were next placed in 100% acetone for 2 minutes. The slides were then air dried.

The tissues fixed to the slides were hybridized to biotinylated chromosome X alpha-satellite DNA probe (ONCOR, Gaithersburg, Md.) by placing a hybridization mixture on the slides. This probe contains repetitive DNA sequences from the centromere region of human chromosome X. The hybridization mixture consisted of the alpha-satellite probe at a concentration of 2 ng/ul of probe in hybridization solution. The hybridization solution consisted of 65% formamide, 2×SSC (0.3M NaCl and 0.03M Nacitrate), 5% dextran sulfate and 100 ug/ml herring testes DNA (Sigma, St. Louis, Mo.).

After the hybridization mixture was placed on the slide, a glass coverslip was placed over the mixture and tissue being careful to not trap air bubbles. The coverslip was sealed to the slide by the application of rubber cement (Carters Rubber Cement, Dennison Manufacturing Co., Framingham, Mass.) around the edges of the coverslip. The rubber cement was allowed to dry at 37° C. for 15 minutes. Freshly applied sealant has a rounded cloudy appearance. When dry, it is flat and translucent.

The probe and target DNA was simultaneously denatured by placing the slide in a 90° C. oven for 12 minutes and the slide was examined to confirm that the seal remained intact. The slides were transferred to a humidified chamber (2×SSC in $CO_2$ incubator) and incubated at 37° C. overnight.

The coverslip sealant was carefully removed with forceps; without removing the coverslip. The slides were washed 2 times in Post-Hybridization Wash Solution (50% formamide, 2×SSC, pH=7.0) at 37° C. for 15 minutes each wash. The slides were agitated 2 to 3 times during these washes to remove the non-specifically bound probe. The slides were then washed in 0.1×SSC for 30 minutes at 37° C. to wash out the formamide.

The slides were next placed in 1×PBD (phosphate buffered detergent) (ONCOR, Gaithersburg, Md.). 1×PBD is 0.05% nonidet P-40 (Sigma), 0.1M $NaPO_4$ pH 8.0. The slides cannot be allowed to air dry beyond this point.

The slides are removed from 1×PBD and the excess fluid removed by blotting the fluid from the edge of the slides. The coverslip was removed. 60 ul of Fluorescein-labeled Avidin solution [5 µg/ml, Fluorescein-labeled Avidin (Vector Laboratories, Burlingame, Calif.) in 1×PBD, 5% nonfat dry milk] was applied to each slide and covered with a plastic coverslip. The slides were then incubated for 20 minutes at room temperature. The coverslip was then carefully peeled back with forceps and the slide tilted to allow the fluid to drain briefly. The slides were washed 3 times in 1×PBD at room temperature for 2 minutes each wash. These washes remove excess and unbound detection compounds.

The coverslip was again peeled back and 60 ul of Anti-avidin antibody (Vector Laboratories, Burlingame, Calif.) 5 µg/ml in 0.1M $NaPO_4$; 0.1% nonidet P-40; 5% normal goat serum (Vector, Laboratories, Burlingame, Calif.) was applied to each slide. The slides were incubated for 20 minutes at room temperature. The slides were washed 3 times in 40 ml of 1×PBD at room temperature for 2 minutes each.

Next the coverslips were again peeled back and drained and 60 ul of Fluorescein-labeled Avidin solution was added to each slide to increase the signal. The slides were incubated at room temperature for 20 minutes. The slides were then washed 3 times in 40 ml of 1×PBD at room temperature for 2 minutes each.

The nuclei on the slides were stained by the addition of 2.5 ug propidium iodide/ml Antifade (Antifade is 1% p-phenylenediamine in 90% glycerol, pH=8–9) to each slide and a glass coverslip was placed on the slide. The slides were then viewed with a fluorescence microscope at an excitation of 450 nm to 490 nm.

FIG. 1 illustrates the slides observed using this method. In FIG. 1 the nuclei of the cells is indicated by an orange color. The probe appears as a yellow dot. The green mass is background fluorescence. FIG. 1a is human placenta tissue without sodium bisulfite pretreatment. FIG. 1b is human placenta tissue pretreated with sodium bisulfite. FIG. 1c is liver tissue without pretreatment and FIG. 1d is liver tissue pretreated with sodium bisulfite. In all cases, the probe used was the X chromosome alpha-satellite repetitive DNA probe (ONCOR, Gaithersburg, Md.).

It was found that in some cases the level of the signal is improved when the tissue is pretreated with sodium bisulfate (FIG. 1). It was also found that the probe bound to the nuclei in both types of fixed tissue.

It is understood that one skilled in the art could modify the conditions described above so as to optimize the results obtained with different types of tissues and different probes.

EXAMPLE 5

Probing Neuroblastoma and Bladder Carcinoma with N-myc and Chromosome 15 Probe

This example describes a method for using a probe to detect single copy DNA sequences in cells by in situ hybridization to fixed tissue and to detect amplification of that DNA sequence in cancer tissue.

Formalin fixed tissue from a neuroblastoma and formalin tissue from a bladder carcinoma, both from human patients having these diseases, were prepared according to the methods disclosed in Example 4 with the following changes.

In both cases, the tissue was pretreated with 20% sodium bisulfite for 10 minutes at 43° C. The tissue was then treated with 250 ug/ml of proteinase K solution for 20 minutes at 37° C.

Separate Probe-Hybridization Mixtures were prepared containing 5 ng/ul of each probe in Hybridization Solution (50% formamide, 2×SSC, 10% dextran sulfate, 1×Denharts Solution (Sigma, St. Louis, Mo.) and 0.625 ug/ul of human placental DNA (ONCOR, Gaithersburg, Md.), 1.75 ug/ul of herring testes DNA (Sigma, St. Louis, Mo.).

Both tissues were denatured in 70% formamide in 2×SSC pH 7.0 at 85° C. for 12 minutes. Next the slides were dehydrated by passing the slide through a series of cold (−20° C.) 70%, 80%, 90%, and 100% ethanol washes, beginning with 70% ethanol for 2 minutes each wash with agitation. The slides were then air dried. The Probe-Hybridization Mixture was then added to the slides. The slides were covered with a glass coverslip and sealed with rubber cement. The slide is incubated at 37° C. overnight.

The coverslips were peeled back as described in Example 4 and the slides were washed with 50% formamide in 2×SSC pH 7.0 at 37° C. for 15 minutes. Then the slides were washed with 2×SSC for 4 minutes at 37° C. This wash was repeated for another 4 minutes.

The signal was detected as described in Example 4, with Fluorescein-labeled Avidin.

In FIG. 2 the nuclei are indicated by an orange color and the probe signal appears as a yellow dot over the orange nuclei. The green mass is background fluorescence.

Figure 2A:
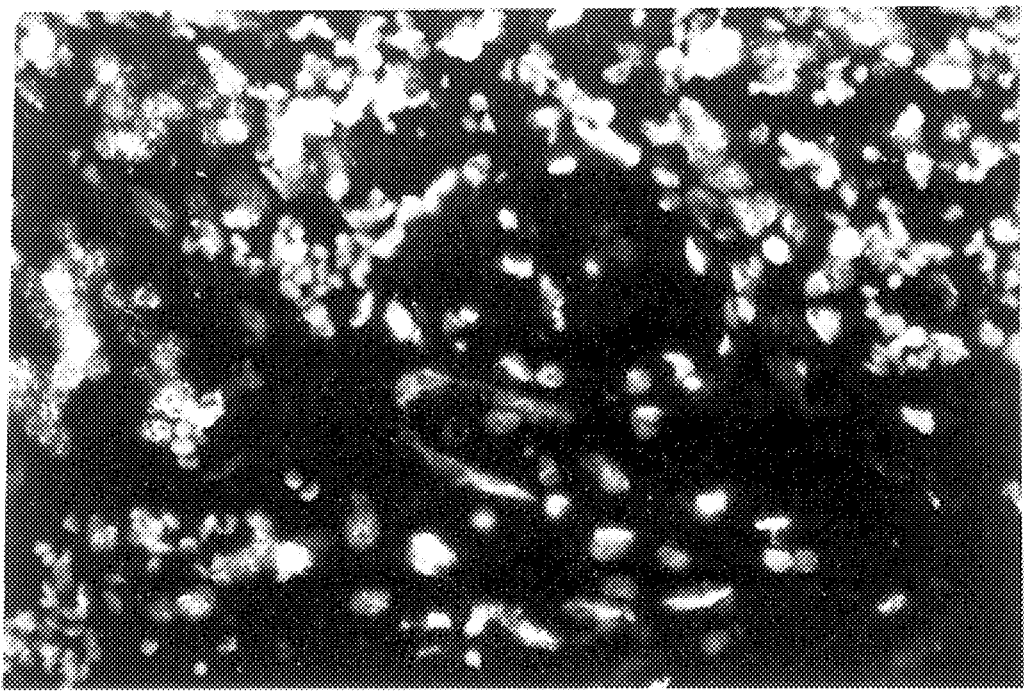
FIG. 2 illustrates the signal pattern of MYCN-113F7 (FIG. 2A) or the chromosome 15 probe (FIG. 2B and 2C) to neuroblastoma tissue.

N-myc is known to be amplified in neuroblastoma tissue by Southern Blot analysis. The neuroblastoma tissue probed with biotinylated MYCN-113F7, by the methods of this example, showed multiple signals over each nuclei indicating that amplified copies of the N-myc gene are present in the neuroblastoma cells. FIG. 2a (40×magnification) shows the binding pattern of the N-myc probe to neuroblastoma tissue. The bladder carcinoma tissue probed with the MYCN-113F7, showed 1 or 2 signals in the occasional cell rather than the multiple signals observed with neuroblastoma tissue.

Figure 2B:
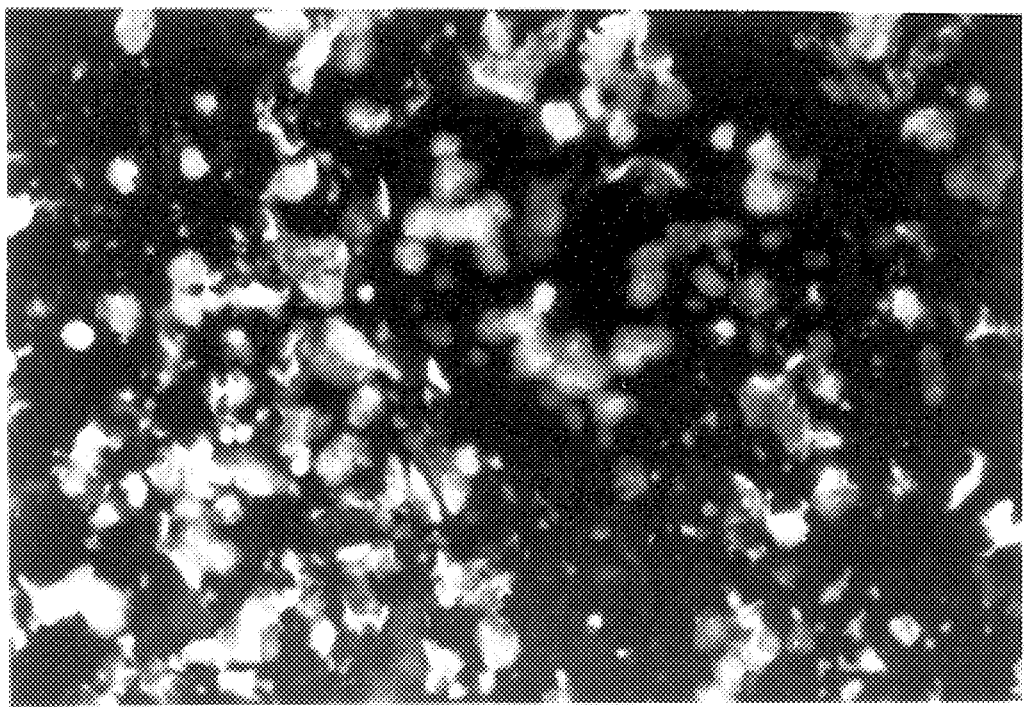
Figure 2C:
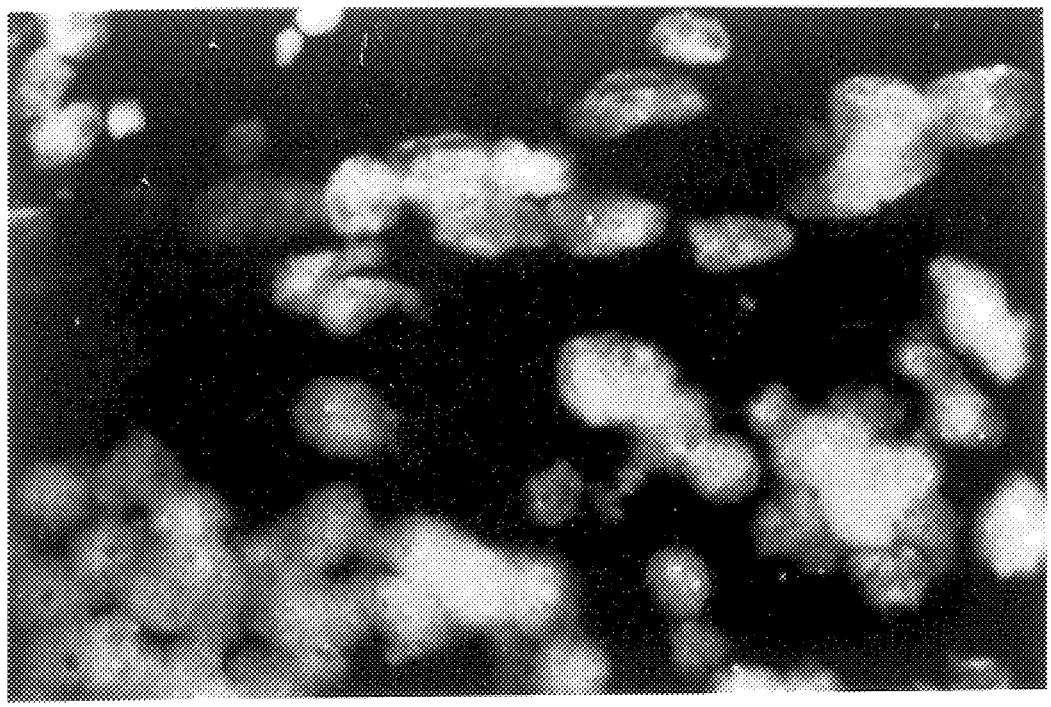

The chromosome 15 probe sequences should not be amplified in neuroblastoma tissue. The neuroblastoma tissue probed with the biotinylated chromosome 15 probe shows the presence of 1 or 2 probe signals per cell nuclei as expected since each cell will contain 2 chromosome 15s. FIG. 2b (40×magnification) and FIG. 2c (100× magnification) show the binding pattern of the chromosomal 15 probe neuroblastoma tissue. The bladder carcinoma tissue probed with the chromosome 15 probe showed multiple copies of the chromosome 15 sequences in the cancerous cells (FIG. 3B).

This example illustrates that the methods disclosed above allow detection of amplification of a single copy gene in fixed tissue samples as well as the absence of amplification. Furthermore, this example illustrates that the method disclosed herein does not result in incorrect signals indicating multiple copies of the single copy sequence in cells lacking amplification.

EXAMPLE 6

Bladder Carcinoma Tissue Probed with Chromosome 15 and X-Chromosome Probes

Bladder carcinoma tissue was obtained from biopsy tissue from a male patient manifesting the disease. The bladder carcinoma tissue was pretreated in 20% sodium bisulfite at 43° C. for 10 minutes.

The tissue was then treated with 250 $\mu$g/ml of Proteinase K solution for 20 minutes at 37° C.

The bladder carcinoma tissue was probed with biotinylated X chromosome alpha-satellite repetitive DNA (Oncor, Gaithersburg, Md.).

The chromosome X alpha-satellite DNA probe was prepared for hybridization to the tissue as follows: 2 ng/$\mu$l of the probe was placed in the Hybridization Solution of Example 4 and the mixture was heated at 85° C. for 10 minutes and then quenched on ice. The Hybridization Mixture was added to the denatured slide and incubated at 37° C. overnight. The denatured slides were prepared as in Example 5.

The chromosome 15 single copy probe was hybridized to the tissue by the method in Example 5.

In both cases, the slides were washed and the signal detected by the methods disclosed in Example 5.

The bladder carcinoma tissue shows multiple copies of the X chromosome indicating aneuploidy for the X chromosome in the abnormal (i.e., cancerous) tissue but only a single copy of the X chromosome in normal cells. Normal cells are elongated whereas cancerous cells are rounded.

Figure 3A:
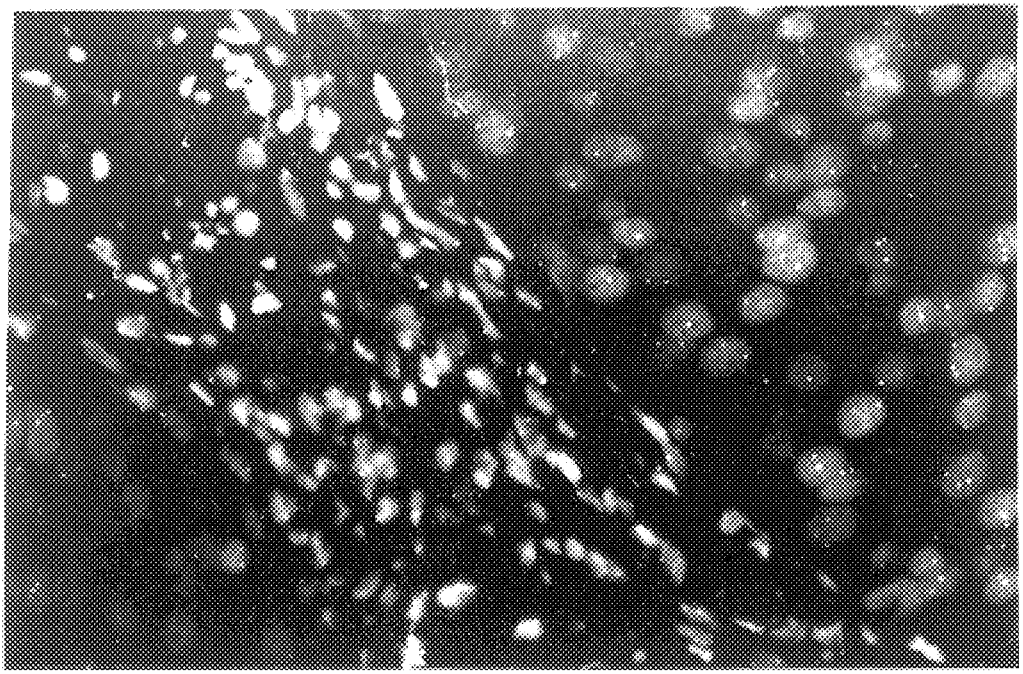
FIG. 3 illustrates the signal pattern of the chromosome 15 probe (FIG. 3A) and the chromosome X alpha-satellite DNA probe (FIG. 3B) to human bladder carcinoma tissue and normal tissue.
Figure 3B:
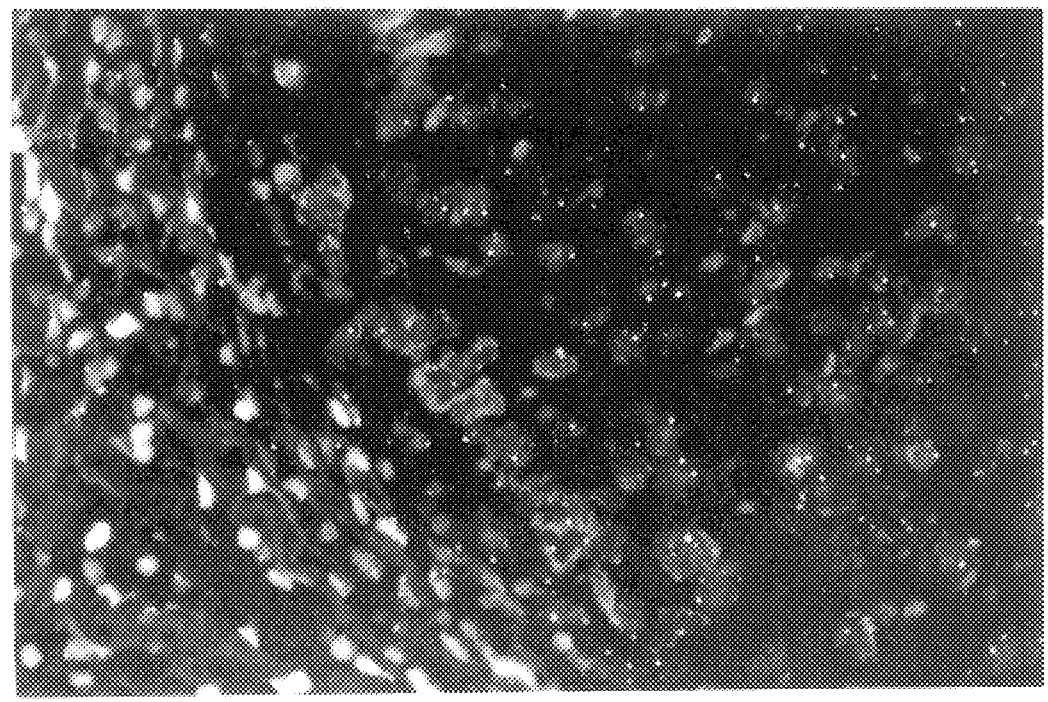

FIG. 3a shows the bladder carcinoma from a male probed with X alpha-satellite.

The bladder carcinoma tissue showed multiple copies of the chromosome 15 sequences in the abnormal (i.e., cancerous) tissue but only two copies of chromosome 15 sequence in the normal tissue. FIG. 3b shows bladder carcinoma from the male probed with the chromosome 15 probe.

EXAMPLE 7

Probing Human Breast Carcinoma Tissue with HER-2/neu

Breast carcinoma specimens were obtained from biopsy tissue from a female patient. The tissue had been fixed in formalin by methods known in the art. The probe was biotinylated HER-2/neu obtained by the method described in Example 2.

The tissue was embedded in paraffin, sectioned, and deparaffinized, as disclosed in Example 4. The tissue did not require sodium bisulfite treatment. The tissues were then treated with 250 µg/ml proteinase K for 30 minutes at 37° C.

The slides were denatured in 70% formamide in 2×SSC pH 7.0 at 85° C. for 12 minutes. The probe hybridization mixture containing 5 ng/µl of probe in the Hybridization Solution described in Example 4 was placed in the slides and the tissue covered with a glass coverslip and sealed with rubber cement. The slides were incubated at 37° C. overnight and then washed as described in Example 5.

The signal was amplified as described in Example 4.

It was observed that the signal was amplified on tumor cells (i.e., more than 2 signals per cell). However, on normal (i.e., non-cancerous cells) the signal was either not present or only two signals were present (i.e., both chromosomes).

While this invention has been described and illustrated herein by references to various specific material, procedures and examples, it is understood that the invention is not restricted to the particular material, combinations of material, and procedures selected for that purpose. Numerous variations of such details can be implied as will be appreciated by those skilled in the art.

---

---

What is claimed is:

1. A method of performing in situ hybridization with a probe which specifically hybridizes to a single copy sequence as a means of detecting a chromosome structural abnormality in a cell from a fixed tissue sample obtained from a patient suspected of having a chromosome structural abnormality wherein said method comprises the steps of:

(a) obtaining a fixed tissue sample from said patient;
   (b) pretreating the fixed tissue sample obtained in step (a) with a bisulfite ion composition;
   (c) digesting the fixed tissue sample with proteinase;
   (d) performing in situ hybridization on cells obtained from the digested fixed tissue sample of step (c) with a probe which specifically hybridizes to a single copy sequence in a critical chromosomal region of interest wherein a signal pattern of hybridized probes is obtained;
   (e) comparing the signal pattern of the hybridized probe in step (d) to a predetermined signal pattern of the hybridized probe obtained when performing in situ hybridization on cells having a normal critical chromosome region of interest; and
   (f) detecting a chromosome structural abnormality in said critical chromosomal region of interest of the patient's cells, by detecting a difference between the signal pattern obtained in step (d) and the predetermined signal pattern.

2. The method of claim 1, wherein the probe is separately detectable.

3. The method of claim 1, wherein the chromosome structural abnormality is a deletion.

4. The method of claim 1, wherein the chromosome structural abnormality is an amplification of a sequence.

5. The method of claim 1, wherein the chromosome structural abnormality is a translocation.

6. The method of claim 1, wherein the chromosome structural abnormality is an inversion.

7. The method of claim 1, wherein the probe is directly labelled.

8. The method of claim 7, wherein the direct label is a radioactive label.

9. The method of claim 8, wherein the radioactive label is $^{32}P$, $^{3}H$ or $^{35}S$.

10. The method of claim 7 wherein the direct label is a non-radioactive label.

11. The method of claim 10, wherein the direct label is a fluorescent dye.

12. The method of claim 11, wherein the fluorescent dye is fluorescein, rhodamine, lucifer yellow, Texas red, or AMCA blue (7-amino-4-methylcoumarin-3-acetate).

13. The method of claim 10, wherein the direct label is a cyanin dye.

14. The method of claim 7, wherein the probe is labelled by:
   (a) synthesizing the probe by incorporating a nucleotide attached to an activated linker arm; and
   (b) adding a detectable marker which binds to the activated linker arm.

15. The method of claim 14, wherein the detectable marker is a fluorescent dye.

16. The method of claim 15, wherein the fluorescent dye is fluorescein, rhodamine, lucifer yellow, Texas red, or AMCA blue (7-amino-4-methylcoumarin-3-acetate).

17. The method of claim 14, wherein the detectable label is a cyanin dye.

18. The method of claim 1, wherein the probe is indirectly labelled.

19. The method of claim 18, wherein the probe is labelled by:
   (a) synthesizing the probe by incorporating a hapten attached to a nucleotide; and
   (b) adding a detectable marker attached to a binding molecule which binds to the hapten.

20. The method of claim 19, wherein the hapten is biotin.

21. The method of claim 20, wherein the binding molecule is avidin.

22. The method of claim 21, wherein the detectable marker is a fluorescent dye.

23. The method of claim 22, wherein the fluorescent dye is fluorescein, rhodamine, lucifer yellow, Texas red, or AMCA blue (7-amino-4-methylcoumarin-3-acetate).

24. The method of claim 21, wherein the detectable marker is a cyanin dye.

25. The method of claim 19, wherein the hapten is digoxygenin.

26. The method of claim 25, wherein the binding molecule is an antibody directed to digoxygenin.

27. The method of claim 26, wherein the detectable marker is a fluorescent dye.

28. The method of claim 27, wherein the fluorescent dye is fluorescein, rhodamine, lucifer yellow, Texas red or AMCA blue (7-amino-4-methylcoumarin-3-acetate).

29. The method of claim 26, wherein the detectable label is a cyanin dye.

30. The method of claim 18, wherein the probe is labelled by:
   (a) synthesizing the probe by incorporating a hapten attached to a nucleotide; and
   (b) adding a binding molecule which binds to the hapten, and to which binding molecule an enzyme producing a detectable signal has been attached.

31. The method of claim 30, wherein the hapten is biotin.

32. The method of claim 31, wherein the binding molecule is avidin.

33. The method of claim 32, wherein the enzyme is alkaline phosphatase or horseradish peroxidase.

34. The method of claim 30, wherein the hapten is digoxygenin.

35. The method of claim 34, wherein the binding molecule is an antibody directed to digoxygenin.

36. The method of claim 34, wherein the enzyme is alkaline phosphatase or horseradish peroxidase.

37. The method of claim 1, wherein said probe is a chromosome 15 probe.

38. A method of enhancing the signal generated using in situ hybridization with a probe for repetitive DNA in a cell from a fixed tissue sample wherein said method comprises the steps of:
   (a) obtaining a fixed tissue sample;
   (b) pretreating the fixed tissue sample obtained in step (a) with a bisulfite ion composition;
   (c) digesting the fixed tissue sample with an effective amount of proteinase;
   (d) performing in situ hybridization on cells obtained from the digested fixed tissue sample of step (c) with a probe for a repetitive DNA sequence in a critical chromosomal region of interest wherein a signal pattern of hybridized probes is obtained;
   (e) comparing the signal pattern of the hybridized probe in step (d) to a predetermined signal pattern of hybridized probe obtained when performing in situ hybridization on cells having a normal repetitive DNA region of interest; and (f) detecting a chromosome structural abnormality in said critical chromosomal region of interest, by detecting a difference between the signal pattern obtained in step (d) and the predetermined signal pattern.

39. A method according to claim 1, wherein the proteinase is proteinase K.

40. A method according to claim 1, wherein the bisulfite ion composition is sodium bisulfite.

41. A method according to claim 38, wherein the proteinase is proteinase K.

42. A method according to claim 38, wherein the bisulfite ion composition is sodium bisulfite.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:1:

CGGCCAAGAT TCCGGGAGTT GGT                    2 3

( 2 ) INFORMATION FOR SEQ ID NO:2:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:2:

TCTTGATGCC AGCAGAAGTC AGGC                   2 4